US007239911B2

(12) United States Patent
Scholz

(10) Patent No.: US 7,239,911 B2
(45) Date of Patent: Jul. 3, 2007

(54) METHOD FOR LOCALIZING AT LEAST ONE FOCAL LESION IN A BIOLOGICAL TISSUE SECTION

(75) Inventor: Bernhard Scholz, Heroldsbach (DE)

(73) Assignee: Siemens Aktiengesellschaft, Munich (DE)

( * ) Notice: Subject to any disclaimer, the term of this patent is extended or adjusted under 35 U.S.C. 154(b) by 410 days.

(21) Appl. No.: 10/614,944

(22) Filed: Jul. 8, 2003

(65) Prior Publication Data

US 2004/0073103 A1 Apr. 15, 2004

(30) Foreign Application Priority Data

Jul. 8, 2002 (DE) .............................. 102 30 813

(51) Int. Cl.
*A61B 5/05* (2006.01)
(52) U.S. Cl. .................................................... 600/547
(58) Field of Classification Search ................ 600/547, 600/407, 587, 372, 382
See application file for complete search history.

(56) References Cited

U.S. PATENT DOCUMENTS 6,308,097 B1 * 10/2001 Pearlman .................... 600/547
6,560,480 B1 * 5/2003 Nachaliel et al. ........... 600/547

FOREIGN PATENT DOCUMENTS

WO WO 99/48422 9/1999

OTHER PUBLICATIONS

Gencer, Nevzat et al. Differential Characterization of Neural Sources with the Bimodal Truncated SVD Pseudo-Inverse for EEG and MEG Mearsurements, Jul. 7, 1998, IEEE Transations on Biomedical Engineering, vol. 45, No. 7, pp. 827-838.*
"Towards Virtual Electrical Breast Biopsy: Space-Frequency MUSIC for Trans-Admittance Data," Scholz, IEEE Trans. on Medical Imaging, vol. 21, No. 6, Jun. 2002, pp. 588-595.

* cited by examiner

*Primary Examiner*—Max F. Hindenburg
*Assistant Examiner*—Fangemonique Smith
(74) *Attorney, Agent, or Firm*—Schiff Hardin LLP

(57) ABSTRACT

In a method for localizing at least one focal lesion in a biological tissue section, the lesion exhibiting an electrical property different from the tissue section, and the electrical property in the tissue section being essentially constant, a sequence of electrical excitation signals having different frequency is supplied to the tissue section, electrical response signals are measured at a number of measuring locations on the surface of the tissue section that occur due to the excitation signals, electrical admittance data are determined from the response signals dependent on the location on the surface, a maximum of the admittance data and the appertaining position of the maximum on the surface are determined, and a depth position of the lesion under the position of the maximum is determined dependent on the position of the maximum.

1 Claim, 4 Drawing Sheets

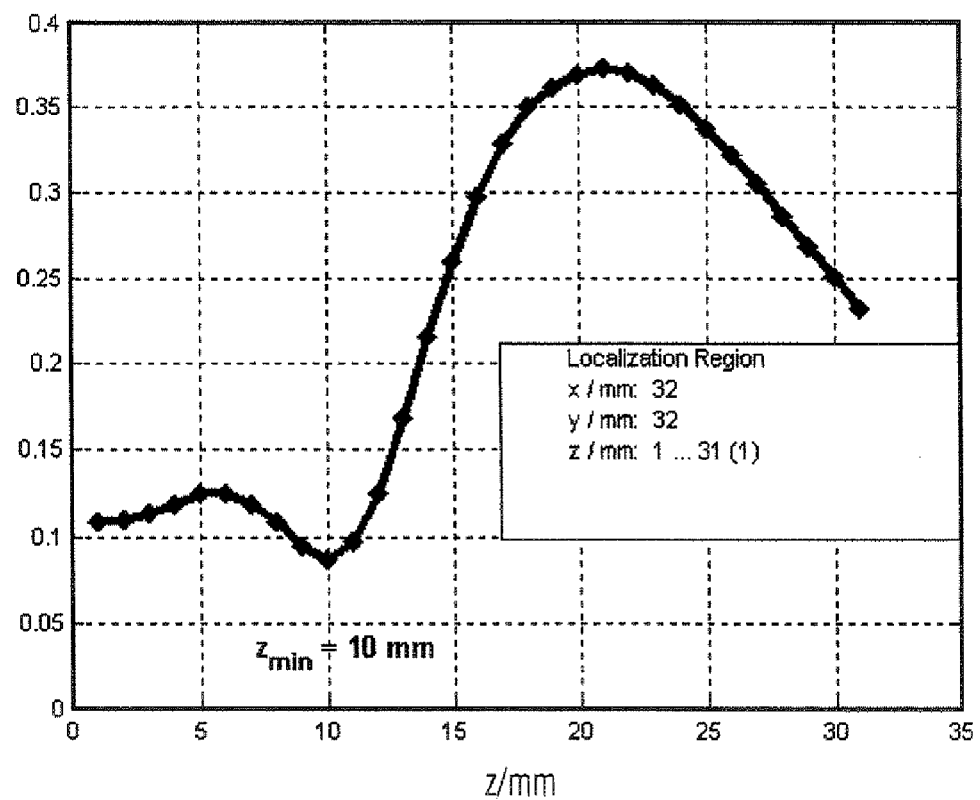

METHOD FOR LOCALIZING AT LEAST ONE FOCAL LESION IN A BIOLOGICAL TISSUE SECTION

BACKGROUND OF THE INVENTION

1. Field of the Invention

The present invention is directed to a method for localizing at least one focal lesion in a biological tissue section, with the lesion exhibiting an electrical property different from the tissue section, and with the electrical property in the tissue section being essentially constant.

2. Description of the Prior Art

A method of the above type is disclosed by PCT Application WO99/48422. For imaging by means of electrical impedance measurement, electrical currents are impressed and/or electrical voltages are applied to an examination subject at one or more locations therein. Voltages that arise due to the impressed currents are measured using M electrodes ($M \geq 1$) that are brought into electrical contact with the tissue section under examination at one or more locations. Alternatively, currents that are established due to the applied voltages are measured either exclusively or additionally as well. The voltages and/or currents are determined by the electrical properties of the subject (described, for example, by the complex conductivity in the mathematical sense). Measured data at m different locations thus are obtained.

The electrical conductivity is composed of a d.c. component and frequency-dependent polarization current components. By analogy to alternating current technology, the electrical conductivity is accordingly mathematically described as a complex quantity.

For example, 64 or 256 time-dependent current values can be measured at present at the surface of the female breast by means of 8×8 or 16×16 regularly arranged electrodes using an apparatus of the TransScan Company that is distributed under the name TS2000. The measurement area amounts to approximately 7.9×7.9 $cm^2$. The measured current values arise due to an alternating voltage between the measuring electrodes and a reference electrode at the contra-lateral hand. The measured data, magnitude and phase of the current are individually converted into conductance values and capacitance values are presented in conformity with the two-dimensional electrode arrangement.

When focal lesions that, for example, exhibit a higher electrical conductivity than the surrounding tissue are situated in the tissue section under the electrode arrangement, then—for example in the case of current measurements—higher current values are measured in the electrodes lying immediately thereabove. Such a lesion is visible as a peak in the two-dimensional measured data presentation. The peak amplitude and the peak width are dependent on the size and depth of the lesion and on the difference in conductivity between the lesion and the surrounding tissue.

SUMMARY OF THE INVENTION

An object of the present invention is to provide a simple and fast method for localizing a focal lesion in a tissue section.

This object is achieved in a method having steps of:

applying a sequence of electrical excitation signals having different frequency to the tissue section, measuring electrical response signals at a number of measuring locations on the surface of the tissue section that occur due to the excitation signals, determining electrical admittance data from the response signals dependent on the location on the surface, and determining a maximum of the admittance data and of the appertaining position on the surface, and determining a depth position of the lesion under the position of the maximum dependent on the position of the maximum.

The localization method is thus limited to only a single coordinate direction.

Any localization method can be employed for the localizing in depth direction, however, the application of a localizing method by means of orthogonal lead fields is especially advantageous. The result of the localizing is the center of gravity of the focal lesion.

DESCRIPTION OF THE DRAWINGS

FIG. 4 is a presentation of the localization function as function of the depth.

DESCRIPTION OF THE PREFERRED EMBODIMENTS

Figure 1:
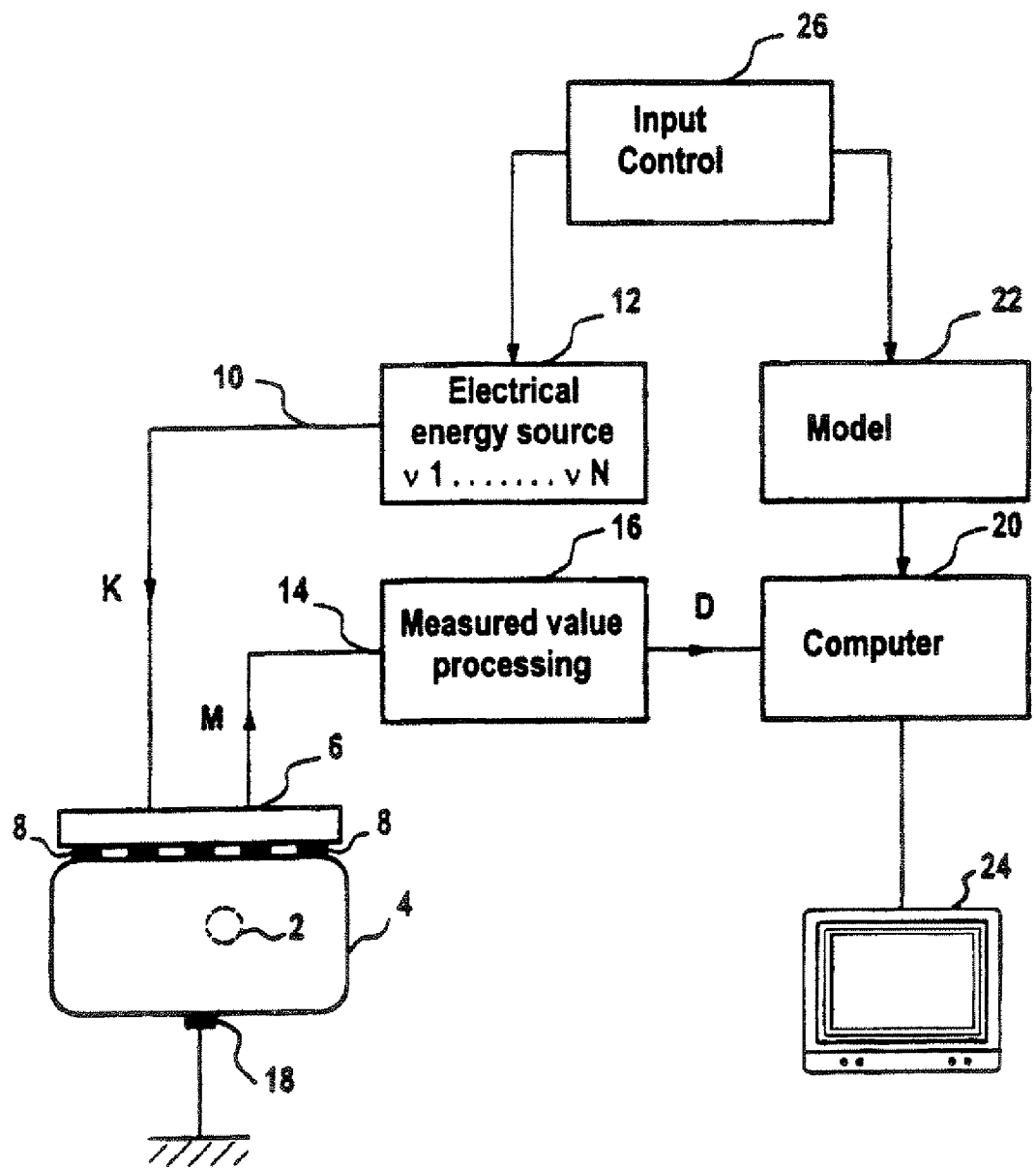
FIG. 1 is an overview presentation showing the basic components of device for localizing and identifying a focal lesion in a tissue section in accordance with the invention.

The overview illustration in FIG. 1 shows a measurement and evaluation arrangement with which signal activities of a limited spatial region 2 can be localized in a biological tissue section 4 and identified. It is assumed that the spatial region 2 has an electrical conductivity different from the surrounding tissue section 4, and that the remaining tissue section 4 exhibits an electrical conductivity that is essentially spatially constant. These assumptions are adequately met when the biological tissue section 4 is a female breast and the limited spatial region 2 is a tumor.

The measurement arrangement includes an applicator 6 having a number of spatially distributed electrodes 8 that are brought into contact with the surface of the tissue section 4. For clarity, only five electrodes 8 are shown in FIG. 1. For an adequately precise localization, however M=256 electrodes 8, for example, should be arranged on an area of, for example, 9×9 $cm^2$.

The electrodes 8 are connected to an electrical energy source (current source or voltage source) 12 via electrical leads 10 and to a measured value editor 16 via electrical leads 14. A cooperating electrode 18 is arranged at that side of the tissue section 4 lying opposite the applicator 6. The cooperating electrode 18 is likewise connected to the current source 12 in the case of potential measurements relative to the voltage source 12, and in the case of current measurements to the measured value editor 16. There is also the possibility of fashioning a part of the applicator 6 as a cooperating electrode.

With the electrical energy source 12, alternating currents (in the case of potential measurements), or alternating voltages (in the case of current measurements) are supplied to the biological tissue section 4 via K electrodes in order to generate a spatial current distribution thereat, whereby $1 \leq K \leq M$ applies. Limited spatial regions 2 that have a different electrical conductivity than the surrounding tissue 4 are electrically polarized by the externally supplied currents or applied voltages such that the polarized spatial regions 2 can be approximately considered as focal bioelectrical signal sources. The respective signal intensity is dependent on the size and on the frequency-dependent, complex conductivity of the spatial region 2 under observation.

The localization and identification of spatially limited regions 2 is reduced to the locating and the determination of the strength of such bioelectrical signal sources by measuring the potentials generated by the supplied currents on the surface of the tissue section 4 at M electrode locations, or the currents generated in the tissue section 4 by the applied voltages are measured at the M electrode locations and are supplied for an evaluation. Since the frequency dependency of the electrical conductivity in the limited spatial regions 2 represents an important quantity for characterizing (classifying) or identifying the corresponding tissue, the current source can generate 12 currents or the voltage source can generate 12 voltages with N different frequencies that, for example, lie in the range from 100 Hz through 500 kHz and are supplied to the tissue section 4.

The measured value editor 16 includes, for example, measuring amplifiers, filters and analog-to-digital converters. The measured value editor 16 is connected to one or more data inputs of an electronic computer 20. In addition to the measured values, a model 22 of the tissue section 4 is made available to the computer 20, the aforementioned bioelectrical signal sources being localized and identified with the assistance of this model 22, as described below. The result, for example in the form of a graphic presentation of the anatomy of the tissue section wherein the location of the signal sources, and thus of the spatial regions 2 is marked, ensues via a monitor 24. Additionally, a quantity characterizing the signal activity is presented at the monitor 24 that is dependent on the current or voltage frequencies. Since the model 22 is determined inter alia by the generated current patterns in the tissue section 4 and the application location, a higher-ranking input and control 26 is provided with which the number and the location of the feed electrodes 8 or of the voltage electrodes 8, the value of the current or voltage frequency, and the model 22 are prescribed.

A localization method is explained as an example below on the basis of FIG. 2. First, the input quantities, i.e. the measured data and the model data, are discussed, followed by the method steps.

Figure 2:
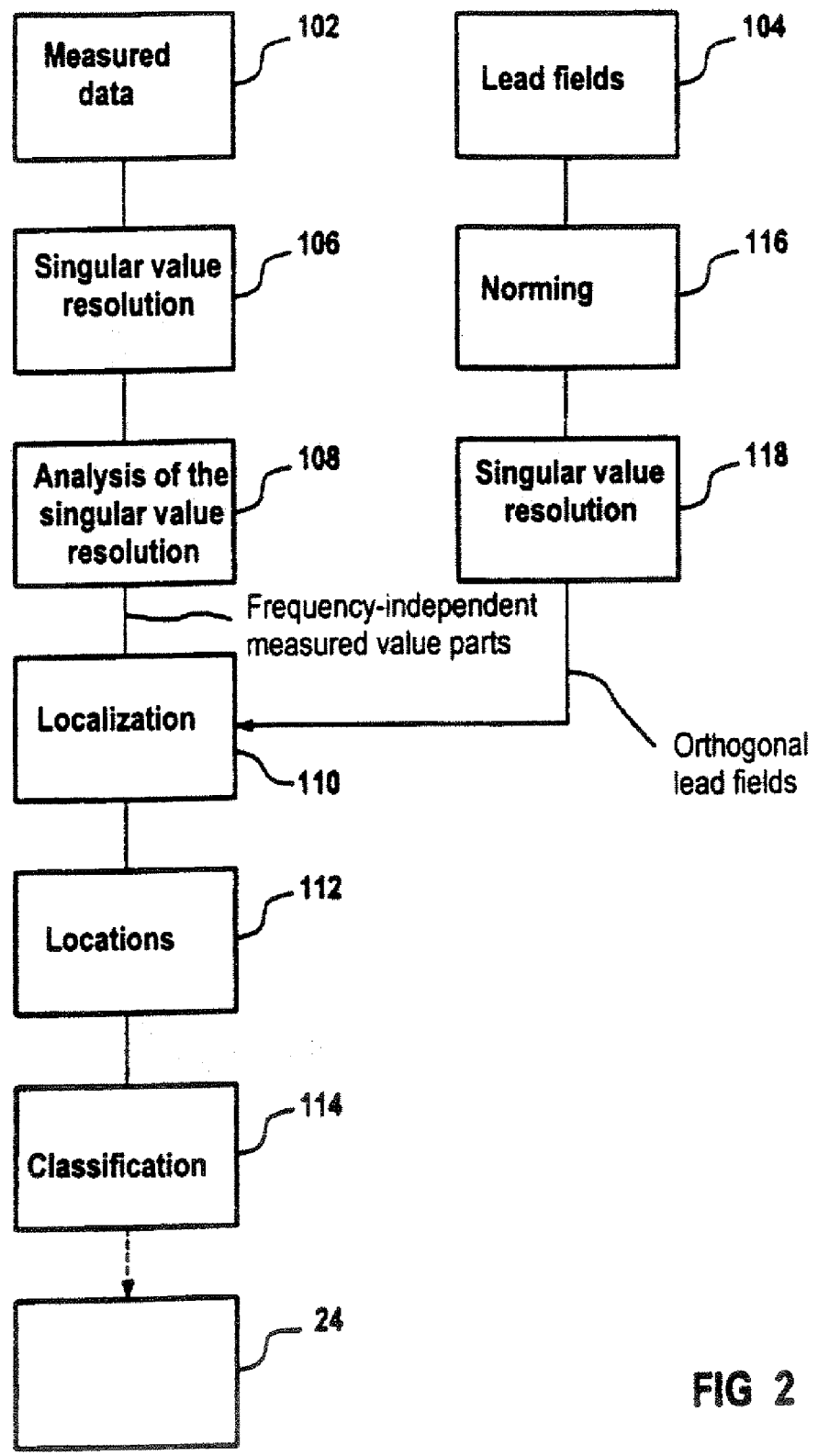
FIG. 2 shows the basic method steps for localizing and classifying a focal lesion in accordance with the invention.
Figure 3A:
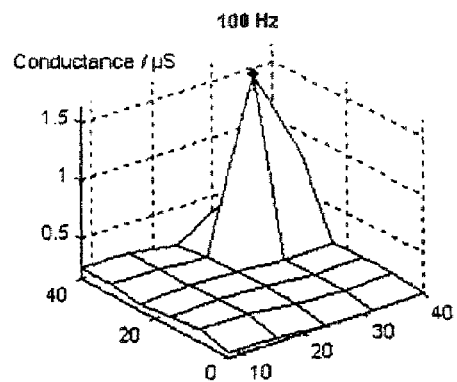
FIGS. 3A through 3D show clinical conductance values of a malignant, focal breast lesion.
Figure 3B:
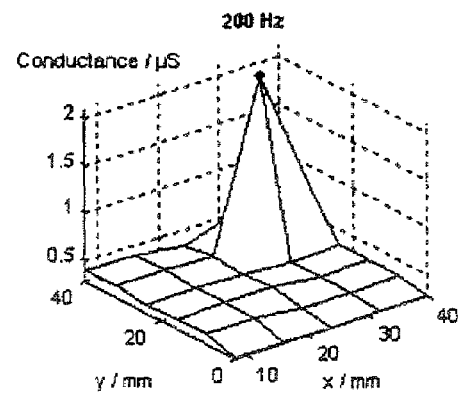
Figure 3C:
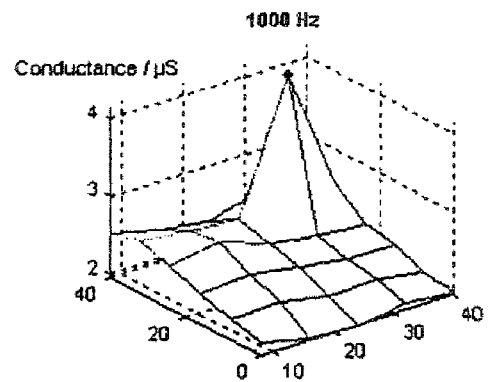
Figure 3D:
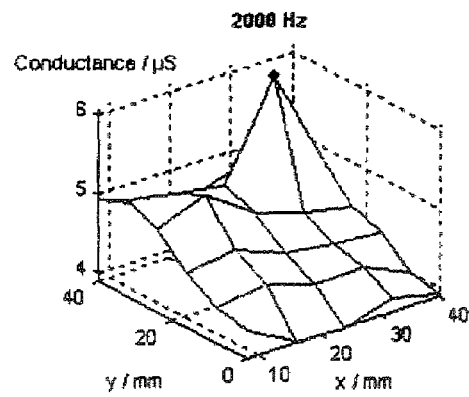

Input quantities for the localizing method are:
a) an M×N data matrix D with measured values (reference character 102) that is dependent on the M electrode locations $\bar{r}_m$,(m=1, ..., M) and on the N current or voltage frequencies $v_n$,(n=1, ..., N).
b) A set of K lead fields $L_k(\bar{r}_i, \bar{r}_m, \bar{n}_m)$, (k=1, ..., K), for example multi-pole lead fields, that are identified in FIG. 2 with reference character 104 and that are in turn dependent on
a volume conductor model of the examination region 4,
a modeling of the conductivity inhomogeneities as bioelectrical signal sources at the location $\bar{r}_i$,
the type of measurement (measurement of potential and/or current), and
on the measurement electrodes 8 in terms of their position $\bar{r}_m$, their surface orientation (which is described by the normal vector $\bar{n}_m$) and their geometrical expanse.

The data D can be current and/or voltage values that were measured at a fixed time with respect to a reference signal, or can be linear combinations of current and/or voltage values that were acquired at a number of times with respect to a reference signal. As a consequence of coefficients that are used in the formation of the linear combinations, the data can be converted into conductance values and/or capacitance values. The following considerations are independent of the measuring time or times. The measurement times therefore have not been included as arguments in the formulaic expressions.

When measured data D are referred to during the course of this exemplary presentation, this means current data that were converted into admittance data. The admittance data can be purely real (only electrical conductance) or purely imaginary (only susceptances) or can be complex (both conductance and susceptance).

The data matrix D can also be derived from a linear combination of at least two datasets. For example, the difference between a dataset with lesion signals and a spatially adjacent dataset without lesion signal can be observed. The amount of the exciting electrical field is clearly reduced in, if not eliminated from the difference data.

It may be necessary to supply post-processed measured data to the localization step. For example, edge artifacts can be eliminated by cutting edge data off. They can simulate a non-existent frequency dependency.

The simplest example of a volume conductor is conductive, infinite space. Here—as well as below—"conductive" recognizes the fact that the conductivity of the medium observed is complex. This means that ohmic as well as dielectric properties are described. Another example of a volume conductor is the conductive, infinite half-space. Both models are patient-independent.

The electrical lead fields for current measurements or potential measurements are the electrical field components or potentials generated by a point source having the intensity of 'one' at the location $\bar{r}_k$ that can be measured with the given measuring arrangement that is defined by the normal vector $\bar{n}_m$ with respect to the $m^{th}$ measurement electrode at the location $\bar{r}_m$.

It is of assistance for the further steps to combine the values of the $k^{th}$ lead field $L_k$(K=1, ..., K) at the M measuring locations to form an M-dimensional vector in the data space (symbolized by the underlining under L).

$$L_k(\bar{r}) \equiv (L_k(\bar{r},\bar{r}_1), \ldots, L_k(\bar{r},\bar{r}_M))^T \text{ with } k=1, \ldots, K \quad (1)$$

wherein $\bar{r}$ is the center of gravity location of the lesion.

The signal processing of the method is composed of
1. the singular value resolution of the data matrix D (reference character 106 in FIG. 2),
2. the analysis of the singular value resolution (reference character 108 in FIG. 2) and
3. the actual localizing (reference character 110 in FIG. 2).

The singular value resolution 106 for the above, generally complex data matrix reads:

$$D = USV^H. \quad (2)$$

The following apply:
U—a unitary M×M matrix that is only dependent on the indices of the electrode locations,
S—the M×N singular value matrix with min (M, N) real singular values in the diagonal and elements that are otherwise disappearing,
V—a unitary N×N matrix that is only dependent on the frequency indices, and
H—indicates the Hermitian conjugation.

The singular values are ordered according to their decreasing numerical size, i.e. the following applies:

$$s_1 \geq s_2 \geq \ldots \geq s_{min(M,N)}. \quad (3)$$

When the $q^{th}$ column vectors of the matrices U and V are referenced with $\underline{u}_q, \underline{v}_q$, then the alternative tonsorial notation ($\otimes$ indicates the tensor product)

$$D = \sum_{q=1}^{\min(M,N)} s_q \underline{u}_q \otimes \underline{v}_q^H \qquad (4)$$

clearly shows that the $q^{th}$ singular value are [sic] exclusively linked with the $q^{th}$ column vectors of U and V. The single and double underlining for u and v are intended to indicate that it is a matter of M-dimensional or N-dimensional vectors.

The M indices of the column vectors $\underline{u}_q$ correspond to the consecutively numbered indices of the quadratically arranged measurement electrodes. Accordingly, these column vectors can be converted into $\sqrt{M} \times \sqrt{M}$-dimensional matrices, and the real/imaginary parts can be presented like two-dimensional measured value distributions. These column vectors are frequency-independent, ortho-normalized base vectors in the M-dimensional data space and are referred to herein as eigenmaps since they can in turn be presented as measured value distribution over the electrode arrangement. In the case of a 16×16 data matrix D, a $\underline{u}_q$ vector is 256-dimensional. Accordingly, it can be entered as a generally complex 16×16 measured value distribution.

The singular value analysis 108 yields the number $Q_{dom}$ of significant singular values and, thus, the number of independent signal sources.

For example, a spherical inhomogeneity in the otherwise homogeneous volume conductor generates a singular value spectrum with two significant singular values ($O_{dom}=2$) when the two conductivity components (environment and sphere) exhibit different frequency behavior.

The appertaining column vectors $\underline{u}_q$ are considered as base vectors of a frequency-independent $Q_{dom}$-dimensional signal space in the M-dimensional data space. The remaining M-$Q_{dom}$ column vectors are then the base vectors of the orthogonal signal space. This space is referred to as noise space in earlier literature.

Seeking focal conductivity inhomogeneities corresponds to the search for locations/center of gravity locations of induced signal sources. This search by means of a computer requires the division into discrete values of the assumed model volume conductor that is intended to mathematically simulate the body region 4 to be examined.

The search strategy is to generate model data with normalized and orthogonalized lead fields at every grid location and to compare these to the frequency-independent signal space acquired from the measured data. The locations at which a distance dimension between signal space and model data space assumes a local minimum are interpreted as locations of actual signal sources, and thus of the lesions 2.

The model data are derived from a post-processing of the lead fields. The post-processing begins with normalization of the K lead fields $\underline{L}_k(k=1, \ldots, K)$ from (1) (processing step 116). The individual leadfields are respectively referenced to their norm, so that the normalized leadfields $\underline{L}_k^{(n)}$ arise as follows:

$$\underline{L}_k^{(n)} = \frac{\underline{L}_k}{\|\underline{L}_k\|} \qquad (5)$$

Orthogonalized leadfields are then acquired by a singular value resolution 118 of the M×K lead field matrix $L^{(n)}$. The normalization is indicated by the index (n).

$$L^{(n)} = (\underline{L}_1^{(n)}, \ldots, \underline{L}_K^{(n)}) = U_L S_L V_L^T \qquad (6)$$

For clarity, the arguments of the leadfields, the location vectors of the source location, have been omitted. The first K column vectors $\underline{U}(\vec{r})_{L,k}, (k=1, \ldots, K)$ of the matrix UL are the source-location-dependent, ortho-normalized leadfields that are sought.

For the localizing 110, a check is made at each location $\vec{r}$ of the divided volume conductor to see how large the distance is between the orthogonalized leadfields $\underline{U}(\vec{r})_{L,k}$ and the signal space. A suitable criterion is the function $$F_k(\vec{r}) = 1 - \sum_{i=1}^{Q_{dom}} (\underline{u}_i^H \cdot \underline{U}(\vec{r})_{L,k})^2. \qquad (7)$$

The initial equation for the derivation of (7) is $$\sum_{i=1}^{Q_{dom}} c_i \underline{u}_i = \underline{U}_{L,k} \quad k = 1, \ldots, K. \qquad (8)$$

When the solution of the coefficient $c_i$ is inserted into the evaluation criterion $$F_k(\vec{r}) = \left| \sum_{i=1}^{Q_{dom}} c_i \underline{u}_i - \underline{U}_{L,k} \right|^2, \qquad (9)$$

then the expression in (7) for $F_k(\vec{r})$ follows.

The actual localization function F is the minimum values of the distances $F_k$. It is defined by $$F(\vec{r}) = \min_k \{F_k(\vec{r})\} \qquad (10)$$

The local minimums of the localization function are ordered monotonously ascending according to their numerical values. The locations that are to be assigned to the first $Q_{dom}-1$ local minimums are considered locations of signal generators. The reduction by one takes into consideration that a significant singular value is caused by the tissue surrounding the signal source. However, local minimums that lie below the noise threshold are excluded as signal locations in the consideration.

The reduction by one is omitted in the case of difference data that eliminate the contribution of the externally excited electrical field.

The localization method described in general above is employed here in order to determine only one dimension of the location of the lesion after the two other coordinate values have been identified in the manner described below.

All peak locations (locations with maximum values of the admittances) are selected in the two-dimensional distributions for a number of exposure frequencies of, for example, 256 admittance data given a measurement arrangement having 16×16 electrodes. It may occur that peaks attenuate or intensify at certain frequencies or in frequency ranges. The determination of peaks can occur in two ways:

Computationally: Determination of the maximums and their 2D coordinates in the measurement plane—referred to as $(x_p, y_p)$ by declaration.

Interactively: Clicking on the peak maximum/maximums in graphic presentations of the measured data on a monitor and—following therefrom—the indication of the appertaining 2D coordinates;

by means of mixing (dot, cross, or the like) into the graphic presentations of the measured data, the computational determination of the maximums can be proposed as a click-on possibility.

The advantageous search for the lesion is composed of the following steps:

Limiting the search to a distance in depth direction (z-direction) under the peak positions identified above; the 3D coordinates of the points on the distance are $(x_p, y_p, z)$ with $z=0, \ldots, z_{max}$, whereby $z=0$ is the z-coordinate of the measurement plane.

Determining the path length, i.e. $z_{max}$, and dividing the search path.

Applying a localization method that is based on the analysis of the multi-frequency measured data, as described above. The results of the search method are the 3D centers of gravity of focal lesions.

As warranted, the determination of the malignant/benign nature of the localize focal lesions follows. The results of this method are the tissue-typical frequency dependencies of the induced multi-pole moments that are to be assigned to the lesions.

A first result is the specification of the spatial positions of the lesion centers of gravity. This result can be graphically visualized on the monitor: for example, 2D plot of the localization function over the depth and marking the minimums as lesion locations and/or marking the locations in 3D presentations of the breast region or in appertaining 2D projection planes and/or marking in fusion images that are acquired by combined ultrasound and/or X-ray mammography exposures.

A second result is the tissue classification on the basis of the tissue-typical frequency behavior of the multi-pole moments of the detected lesions. The frequency behavior of the multi-pole moments can be graphically displayed on the monitor in various ways. These, for example, can be:

(1) 2D plot of the multi-pole moments (real/imaginary part and/or amount/phase) over the frequency or (2) Marking (for example, color coding) the lesion locations In the visualizations recited under (a) dependent on multi-pole result (for example, benign=green, malignant=red).

FIGS. 3A through 3D show clinical conductance value data of a malignant, focal breast lesion (recorded with the TS2000 system of the TransScan company) at a depth of 13 mm.

An algorithmic search of the position of the lesion at the peak location in the depth direction follows (virtual electrical biopsy).

For example, the search result can be presented as indicated in FIG. 4. The z-direction here corresponds to the depth direction in which the search is carried out. A lesion center of gravity was found at a depth of 10 mm.

The multi-pole moments at the location of the lesion are then determined in the next step. Only those multi-pole moments whose contributions to the measured signal lie above the noise level are thereby identified.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for localizing at least one focal lesion in a biological tissue section, said lesion exhibiting an electrical property different from the tissue section, and the electrical property in the tissue section being essentially constant, comprising the steps:

applying a sequence of electrical excitation signals respectively having different frequencies to the tissue section;

measuring electrical response signals respectively at a plurality of measuring locations on a surface of the tissue section that occur due to the excitation signals, said surface having surface directions defining said surface;

determining electrical admittance data from the response signals dependent on said surface directions;

determining a maximum of the admittance data, and a position, relative to said surface directions on the surface corresponding to said maximum; and using orthogonal leadfields, determining a depth position of the lesion beneath the position of the maximum dependent on the position of the maximum.

* * * * *